(12) United States Patent
Okada et al.

(10) Patent No.: US 8,728,089 B2
(45) Date of Patent: May 20, 2014

(54) ENDOSCOPE TREATMENT INSTRUMENT

(75) Inventors: Tsutomu Okada, Tokyo (JP); Kosuke Motai, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1258 days.

(21) Appl. No.: 12/057,841

(22) Filed: Mar. 28, 2008

(65) Prior Publication Data

US 2009/0247822 A1   Oct. 1, 2009

(51) Int. Cl.
*A61B 1/00* (2006.01)

(52) U.S. Cl.
USPC ........................................................ 606/106

(58) Field of Classification Search
None
See application file for complete search history.

(56) References Cited

U.S. PATENT DOCUMENTS

| | | | | |
|---|---|---|---|---|
| 3,749,085 A | * | 7/1973 | Willson et al. | 600/570 |
| 4,982,727 A | | 1/1991 | Sato | |
| 5,372,124 A | | 12/1994 | Takayama et al. | |
| 6,443,909 B1 | | 9/2002 | Ouchi | |
| 2004/0220565 A1 | * | 11/2004 | Bales et al. | 606/47 |
| 2005/0277949 A1 | * | 12/2005 | Que et al. | 606/127 |
| 2010/0160952 A1 | * | 6/2010 | Leeflang et al. | 606/198 |

FOREIGN PATENT DOCUMENTS

| | | |
|---|---|---|
| DE | 37 04 094 A1 | 8/1988 |
| EP | 1 561 413 A1 | 8/2005 |
| JP | 55109501 U | 7/1980 |
| JP | 177703 U | 5/1989 |
| JP | 03-047246 | 2/1991 |
| JP | 4120710 U | 10/1992 |
| JP | 55105 U | 1/1993 |
| JP | 55106 U | 1/1993 |
| JP | 7-289549 A | 11/1995 |
| JP | 10165361 A | 6/1998 |
| JP | 2000-229084 | 8/2000 |
| JP | 2004527360 A | 9/2004 |
| JP | 2005204998 A | 8/2005 |
| JP | 2008-48850 A | 3/2008 |
| WO | 02098313 | 12/2002 |
| WO | 2007/089676 A1 | 8/2007 |

OTHER PUBLICATIONS

European Search Report dated May 7, 2013 from corresponding European Patent Application No. EP 11 006 136.3.
Japanese Office Action dated Mar. 5, 2013 issued in corresponding Application No. 2008-317401 together with an English Language Translation.
Notice of Reasons for Rejection dated Oct. 22, 2013 from related Japanese Application No. 2008-317401, together with an English language translation.

* cited by examiner

*Primary Examiner* — Gary Jackson
*Assistant Examiner* — Scott T Luan
(74) *Attorney, Agent, or Firm* — Scully, Scott, Murphy & Presser, P.C.

(57) ABSTRACT

An endoscope treatment instrument provided with a flexible transmitting member, a treatment portion that is attached to the distal end of the transmitting member, and an actuator which is attached to the proximal end of the transmitting member and is for operating the treatment portion, this endoscope treatment instrument being designed to transmit the action of the actuator to the treatment portion via the transmitting member. The transmitting member consists of the connection in the longitudinal direction of a first coil sheath that has excellent rotation follow-up and good relative bending properties, and a second coil sheath that has excellent rotation follow-up and good ease of motion in the relative longitudinal direction.

4 Claims, 16 Drawing Sheets

ENDOSCOPE TREATMENT INSTRUMENT

BACKGROUND OF THE INVENTION

1. Field of the Invention

The present invention relates to an endoscope treatment instrument that is a treatment instrument employed in combination with a flexible endoscope for example, this endoscope treatment instrument being provided with a sheath that has both the property of rotational follow-up as well as the characteristics required of a sheath equipped with a treatment portion.

2. Description of Related Art

Endoscope treatment instruments that are employed by insertion into the channel of a flexible endoscope conventionally include such examples as dissection instruments, grasping forceps, etc. In such endoscope treatment instruments, various treatment portions such as a forceps cup or jaws, or an electrode part composing a dissection part etc., are formed at the distal end of a flexible sheath. As a method for adjusting the orientation of the treatment portion in these endoscope treatment instruments, the proximal end of the sheath is rotated and this rotational force is transmitted via the sheath to the treatment portion at the distal end, thereby rotating the treatment portion.

In the endoscope treatment instrument disclosed in Japanese Patent Application, First Publication No. 2000-229084, for example, an operating wire is inserted into an entire length of the flexible sheath that is inserted into a channel, a forceps cup which can be opened and closed is provided to the distal end side of the operating wire, and an actuator is provided at the proximal end side of the operating wire. The sheath is formed of a multiple layer coil in which two coil pipes which is wound in opposite directions and is overlapped each other. The proximal end of the sheath is fixed in place to the actuator. By rotating the rotation operating pin of the actuator in the axial direction of the sheath, the operating wire and the sheath rotate, so that the forceps cup rotates in the axial direction of the sheath.

The device disclosed in Japanese Patent Application, First Publication No. Hei 3-47246 is provided with a sheath consisting of a flexible and tightly wound coil, a treatment portion such as a biopsy cup provided at the distal end of the sheath, and an actuator which is provided on the handheld side of the sheath. In this device, the movement of the actuator is transmitted to the treatment portion via an operating wire which is inserted into the sheath. The sheath is provided with three types of tightly wound coils: a single strand apex coil, a single strand intermediate coil that has a thicker diameter than the apex coil, and a multiple strand rear end coil. The hardness of the sheath gradually increases from the apex to the rear. Further, by sliding the slider that is provided to the actuator forward and back, a treatment portion can be opened or closed. In addition, the sheath rotates by rotating the actuator for the treatment instrument, thereby enabling the orientation of the treatment portion to be changed.

As a method for adjusting the orientation of the treatment portion that is provided to the distal end of the sheath in these endoscope treatment instruments, the actuator and the proximal end of the sheath are rotated, and this rotational force is transmitted to the treatment portion via the sheath, thereby adjusting its orientation.

However, a sheath equipped with a treatment portion is typically required that the distal end part (within the range of 200 mm from the proximal end of the treatment portion, for example) which overlaps the bending part of the endoscope, be flexible. For this reason, a design in which a multiple layer coil is employed over the entirety of the sheath; a design in which a single strand apex coil, a single strand intermediate coil with a wider diameter than the apex coil, and a multiple strand rear coil are connected so that the hardness gradually increases from the distal end to the proximal end of the sheath; or a design in which a regular single strand coil is connected to the distal end of a multiple strand coil; such as described above, are employed.

However, in a sheath in which the entirety of the sheath consists of a multiple layer coil, since whole of the sheath is flexible, the rotation follow-up property of the sheath is good but the response of this sheath is poor when advancing or retracting the sheath. Further, in the case of sheaths in which a single strand intermediate coil and a multiple strand rear coil are connected so that the hardness gradually increases from the single strand coil provided at the distal end, toward the proximal end side, and sheaths in which a regular single strand coil is connected to the distal end of a multiple strand coil, the excellent rotation follow-up property of the multiple strand coil is nullified by the poor rotation follow-up property of the single strand coil portion at the distal end in these cases.

SUMMARY OF THE INVENTION

The endoscope treatment instrument according to the present invention is provided with a flexible transmitting member, a treatment portion that is attached to the distal end of the transmitting member, and an actuator which is attached to the proximal end of the transmitting member and is for operating the treatment portion, this endoscope treatment instrument being designed to transmit the action of the actuator to the treatment portion by the transmitting member. The endoscope treatment instrument according to the present invention is characterized in that the transmitting member consists of the connection in the longitudinal direction of a first coil sheath that has high rotation follow-up property and high relative bending properties, and a second coil sheath that has high rotation follow-up property and good ease of motion in the relative longitudinal direction.

It is preferable that the first coil sheath be connected on the treatment portion side, and the second coil sheath be connected on the proximal end side of the first coil sheath, in the transmitting member of the endoscope treatment instrument according to the present invention.

Alternatively, in the transmitting member in the present invention, it is also acceptable that respective first coil sheath be connected to the treatment portion side and the actuator side, and that a second coil sheath be connected between these first coil sheath.

In the endoscope treatment instrument according to the present invention, it is preferable that the first coil sheath be formed of a multiple layer coil and the second coil sheath be formed of a multiple strand coil. Further, it is preferable that the multiple layer coil be formed of a single strand coil or a multiple strand coil, and the multiple strand coil be a single layer coil.

The endoscope treatment instrument according to the present invention is provided with a flexible transmitting member, a treatment portion that is attached to the distal end of the transmitting member, and an actuator which is attached to the proximal end of the transmitting member and is for operating the treatment portion, this endoscope treatment instrument being designed to transmit the action of the actuator to the treatment portion via the transmitting member, and being characterized in that the treatment portion is a high-frequency treatment instrument, and in that the actuator is a provided with a sliding body that is electrically connected to the high-frequency treatment instrument via the transmitting member, a support that is electrically connected to a connector, and a ratchet mechanism that is provided to enable electrical conduction or interruption between the sliding body and the support.

The ratchet mechanism may be provided with ratchet teeth that are provided to one of either the sliding body and the support, and a ratchet claw that is provided to the other of the sliding body and the support, and which can engage with the ratchet teeth.

Preferably, the sliding body is connected to the transmitting member, and the treatment portion can be advanced and/or retracted via the transmitting member, by advancing and/or retracting the sliding body in a state that the ratchet teeth and the ratchet claw are engaged.

It is preferable that the operating member that is provided with one of either the ratchet claw and ratchet teeth be provided to the sliding body in a manner which permits advancing and retracting, and that the operating member be biased by an elastic member in a direction so as to cause engagement between the ratchet claw and the ratchet teeth and permit electrical conduction, and that the electrical current be interrupted by separating the ratchet claw and the ratchet teeth by moving the operating member in the direction that is opposite the biasing force of the elastic member

DETAILED DESCRIPTION OF THE INVENTION

The endoscope treatment instrument according the first embodiment of the present invention will now be explained with reference to FIGS. 1 through 4.

Figure 1:
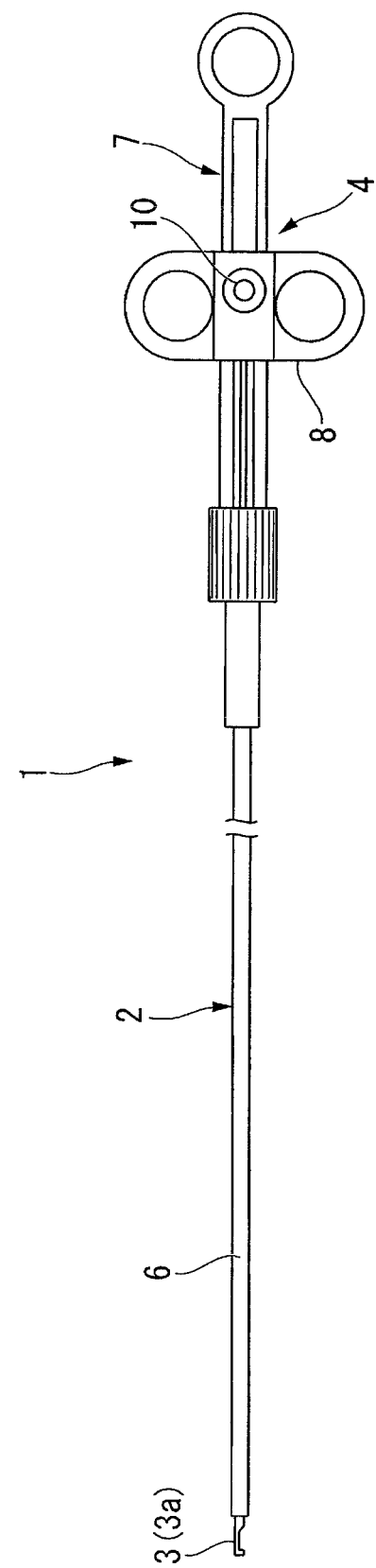
FIG. 1 is a view showing the dissection instrument according to a first embodiment of the present invention.
Figure 2:
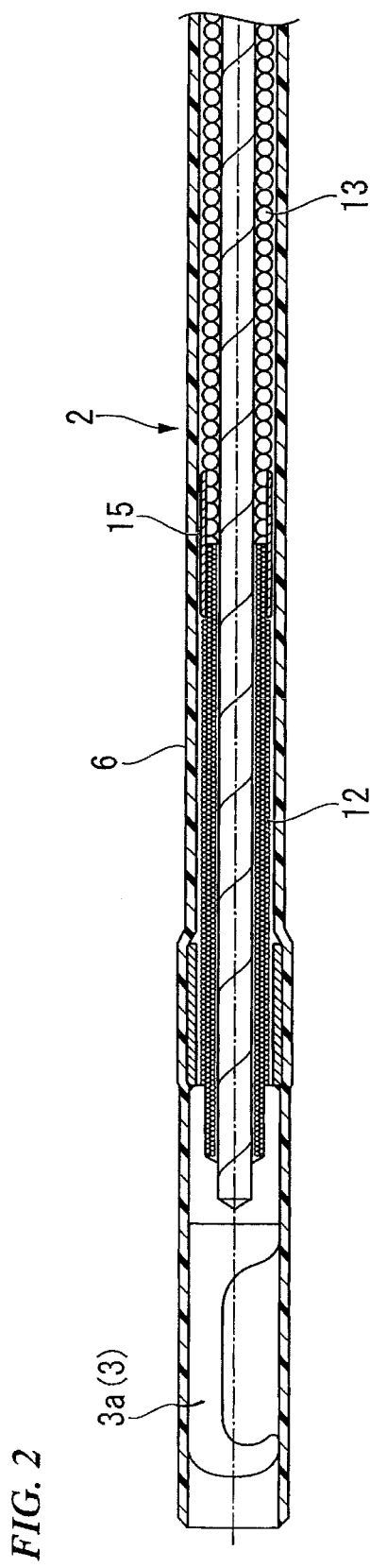
FIG. 2 is a partial cross-sectional view showing the inserted part when the high-frequency hook of the dissection instrument shown in FIG. 1 is housed inside the tube.

FIGS. 1 and 2 show a soft dissection instrument 1 which is the endoscope treatment instrument according to the first embodiment. This dissection instrument 1 is provided with a flexible inserted part 2, a treatment portion 3 attached to the distal end of the inserted part 2, and an actuator 4 connected to the proximal end of the inserted part 2.

The inserted part 2 includes a tube 6 in which a flexible shaft, such as a coil sheath, is inserted into, and can be advanced into a body cavity by insertion into the instrument channel of the endoscope. The treatment portion 3 is a dissection portion, and provided with, for example, a high-frequency hook 3a as a hook consisting of an electrode. The actuator 4 which is provided to the proximal part of the inserted part 2 is provided with a main body 7 extending in the extended direction of the inserted part 2, and a slider 8 which can slide with respect to the main body 7. A connecting part 10 which can be connected to a high-frequency power source is provided to the slider 8, and is electrically conductive with the high-frequency hook 3a via the shaft.

In the inserted part 2 shown in FIG. 2, a multiple layer coil having conductive property, three-layer coil 12 for example, is disposed to the proximal part of the high-frequency hook 3a as the distal shaft. The three-layer coil 12 is formed by winding a metal wire in three layers in the radial direction such as shown in the expanded view in FIG. 3A, and extends to a length of approximately 200 mm, for example. Multiple layer coils, including three-layer coil 12, have high rotation follow-up property and are softer and have better bending properties as compared to multiple strand coils. When the inserted part 2 is inserted into a body cavity, the three-layer coil 12 can form a curved part that can bend or curve in order to incise, etc. the diseased area using the high-frequency hook 3a.

Figure 3A:
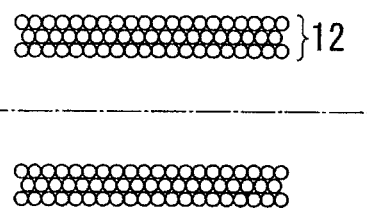
FIG. 3A is a partial expanded cross-sectional view showing the three-layer coil of the transmitting member shown in FIG. 2
Figure 3B:
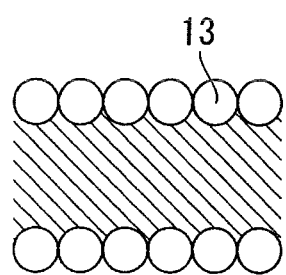
FIG. 3B is a partial expanded cross-sectional view showing a nine-strand coil of the transmitting member shown in FIG. 2.
Figure 4:
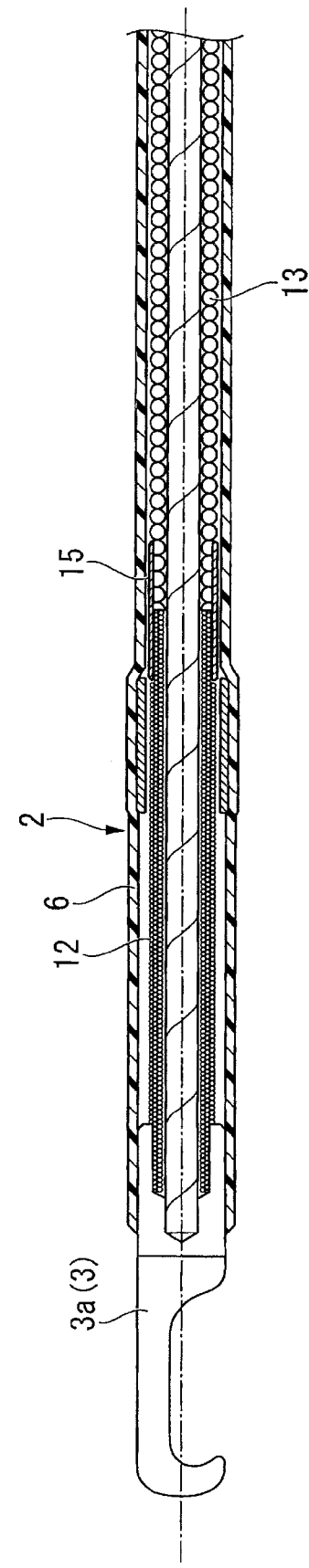
FIG. 4 is a cross-sectional view showing the inserted part when the high-frequency hook has been projected out from the tube.

A conductive single layer, multiple strand coil, as a long shaft, the length of which is greater than that of the three-layer coil 12, nine-strand coil 13 for example, is connected to the proximal end side of the three-layer coil 12. The nine-strand coil 13 is formed by aligning and winding a plurality (nine here) of metal wires as shown in FIG. 3B. As in the case of multiple layer coils, multiple strand coils, including the nine-strand coil 13, has high rotation follow-up property as compared to a single strand coil, and has the property of greater rigidity as compared to multiple layer coils, including the three-layer coil 12. Multiple strand coils also have a good responsiveness when moving in an advanced or retracted direction. The slider 8 is connected to the proximal end of the nine-strand coil 13 by soldering or other such methods. Note that the connection of the three-layer coil 12 which is connected with the multiple strand coil 13 constitutes a shaft.

As a result, the hook 3a can be projected out from the tube 6 via the nine-strand coil 13 and the three-layer coil 12 (see FIG. 4) by advancing the slider 8 along the main body 7 (i.e., moving slider 8 toward the hook 3a side) in the actuator 4, and can be housed within the tube 6 by retracting the slider 8 along the main body 7 (see FIG. 2) in the actuator 4. Further, by rotating the actuator 4, the hook 3a can be rotated by a specific angle via the nine-strand coil 13 and the three-layer coil 12.

Note that the connecting part between the three-layer coil 12 and the nine-strand coil 13 may be formed as follows, for example. In FIG. 2, the outer peripheral surfaces near the connection part between the three-layer coil 12 and the nine-strand coil 13 are cut out to provide step portions to the outer diameters. The respective step portions of the three-layer coil 12 and the nine-strand coil 13 are inserted into a cylindrical connecting tube 15 which has the same outer diameter as the three-layer coil 12 and the nine-strand coil 13, and engage therewithin. And then, soldering material is injected into the boundary area between the three-layer coil 12 and the nine-strand coil 13 via a through hole (not shown in the figures) that passes through the connecting tube 15. The inner surface of the connecting tube 15, and the boundary area between the three-layer coil 12 and the nine-strand coil 13, are thus connected by soldering. As a result, the three-layer coil 12 and nine-strand coil 13, and the connecting tube 15, have approximately same outer diameter over the entire length.

The dissection instrument 1 according to this embodiment is provided with the above-described design. The effects thereof will now be described.

First, the inserted part 2 and the treatment portion 3a of the dissection instrument 1 are inserted into a body cavity via the instrument channel of an endoscope, which is not shown in the figures. By advancing or retracting the slider 8 of the actuator 4 with respect to the main body 7 (see FIG. 4) after projecting out the dissection instrument 1 from the distal end of the endoscope, the high-frequency hook 3a is made to project out from the tube 6. In this case, since the inserted part 2, with the exception of its distal end part, is formed of the long nine-strand coil 13, it can be projected forward with high responsiveness. Further, the three-layer coil 12 on the distal end side is short in length, so that it has only a slight effect on responsiveness. The tissue is then incised by bringing the high-frequency hook 3a, which current is flowing, into contact with the target tissue inside the body cavity.

The actuator 4 may be rotated in the case where the high-frequency hook 3a does not have the desired orientation with respect to the tissue. The rotational force from rotating actuator 4 is transmitted via the nine-strand coil 13 and the three-layer coil 12 inside the tube 6, causing the high-frequency hook 3a to rotate and be positioned with the desired orientation. Moreover, since the distal end parts (of the shaft) is formed of the highly flexible three-layer coil 12, even if the distal end part of the inserted part 2 is bent, the rotation of the long nine-strand coil 13 can be transmitted to the high-frequency hook 3a with certainty without affecting on the bending posture of the endoscope.

In the dissection instrument 1 according to the embodiment described above, the rotation follow-up property over the entire length of the inserted part 2 is high, and the dissection instrument 1 can be advanced or retracted in high responsiveness by the long nine-strand coil 13. Further, the distal end part of the inserted part 2 is a three-layer coil 12 so that the bending of the distal end part of the endoscope can be carried out smoothly. Further, transmission of the rotation to the high-frequency hook 3a when in the bent state can be carried out with certainty.

Next, another embodiment of the present invention will be explained. Note that parts that are identical or similar to that of the first embodiment will be assigned the same numeric symbol and an explanation thereof will be omitted.

The endoscope treatment instrument according to the second embodiment will be explained with reference to FIGS. 5 through 14. In the explanatory view of the medical treatment endoscope shown in FIG. 5, a medical treatment endoscope 20 is provided with an endoscope inserted part 28, the proximal end side thereof being attached to a base via a branch connection 22c. A first sheath 22 and a second sheath 27 are branched and extend from the proximal end side of the branch connection 22c. An actuator 21 of the medical treatment endoscope is provided to the proximal end of the first sheath 22. As shown in FIG. 13, an actuator 65 for operating the jaws 26a of the gripping forceps 26, and an actuator 24 for operating the high-frequency hook 3a of the dissection instrument 23 are disposed in alignment at a specific angle in this actuator 21 of the medical treatment endoscope. These actuators 65,24 are designed to be operated by gripping with the left and right hands respectively.

A plurality of individual channels are provided in the space between the actuator 21 of the medical treatment endoscope, the first sheath 22 and the opening at the distal end of the endoscope inserted part 28. The inserted part 25 of the dissection instrument 23 according to the second embodiment of the present invention and the inserted part (not shown) of the gripping forceps 26 are inserted respectively into these channels.

A separate channel is provided within the second sheath 27 and the endoscope inserted part 28. An irrigation and suction tube 30 is inserted into this separate channel via a stopper 29 that is provided in the proximal end side of the second sheath 27, and projects out from the opening at the distal end. An irrigation and suction device 31, for example, for performing irrigation and suction, is provided at the proximal end of the irrigation and suction tube 30.

Figure 14:
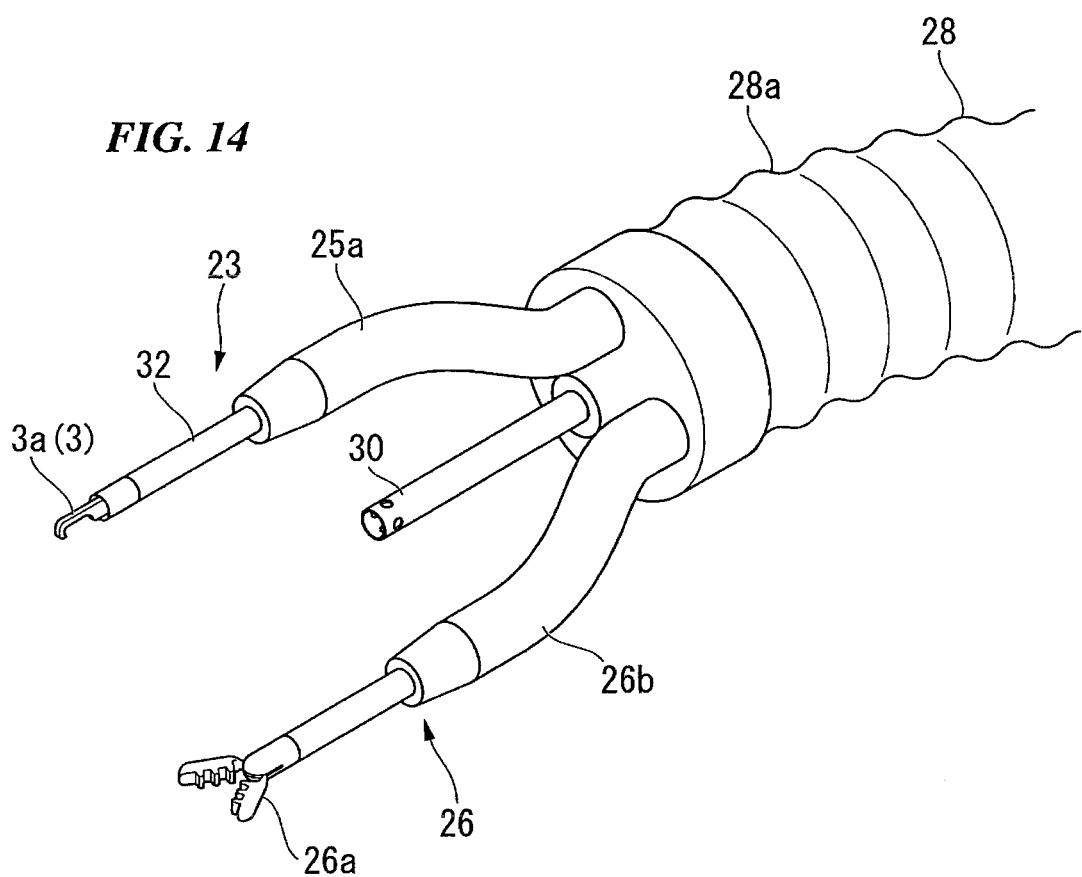
FIG. 14 is a perspective view of the treatment portion that projects out from the opening at the distal end of the medical treatment endoscope shown in FIG. 8.
Figure 15:
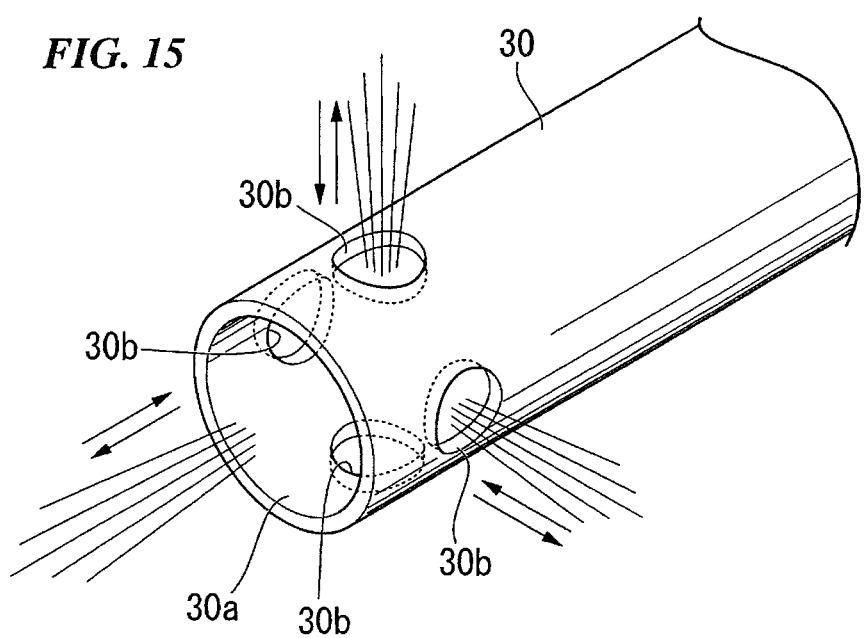
FIG. 15 is an expanded perspective view showing the distal end of the irrigation and suction tube shown in FIG. 5.

As shown in FIG. 14, an arm 25a and an arm 26b are provided at the distal end of the endoscope inserted part 28. The high-frequency hook 3a of the dissection instrument 23 and the jaws 26a of the gripping forceps 26 project out respectively from the distal end of each of the arms 25a, 26b. The irrigation and suction tube 30 projects out from the opening of the separate channel at the distal end of the endoscope inserted part 28. As shown in FIG. 15, a main opening 30a is opened at the distal end and one or more side openings 30b are opened to the sides of the irritation and suction tube 30. The irrigation and suction tube 30 can irrigate to wash away hemorrhage at the diseased area K inside the body cavity, and expelling fluid from the main and side openings 30a,30b, or can suction and recover water, etc. that has accumulated at the diseased area K.

Note that a proximal end side bending part 22a is formed to the first sheath 22, and a distal end side bending part 28a is formed to the endoscope inserted part 28 at its distal opening side. The presence or absence of the respective bending parts 22a,28a of the first sheath 22 and the endoscope bending part 28 depends on the position of attachment and the method of use, and it is not absolutely essential that the parts be bent.

Figure 6:
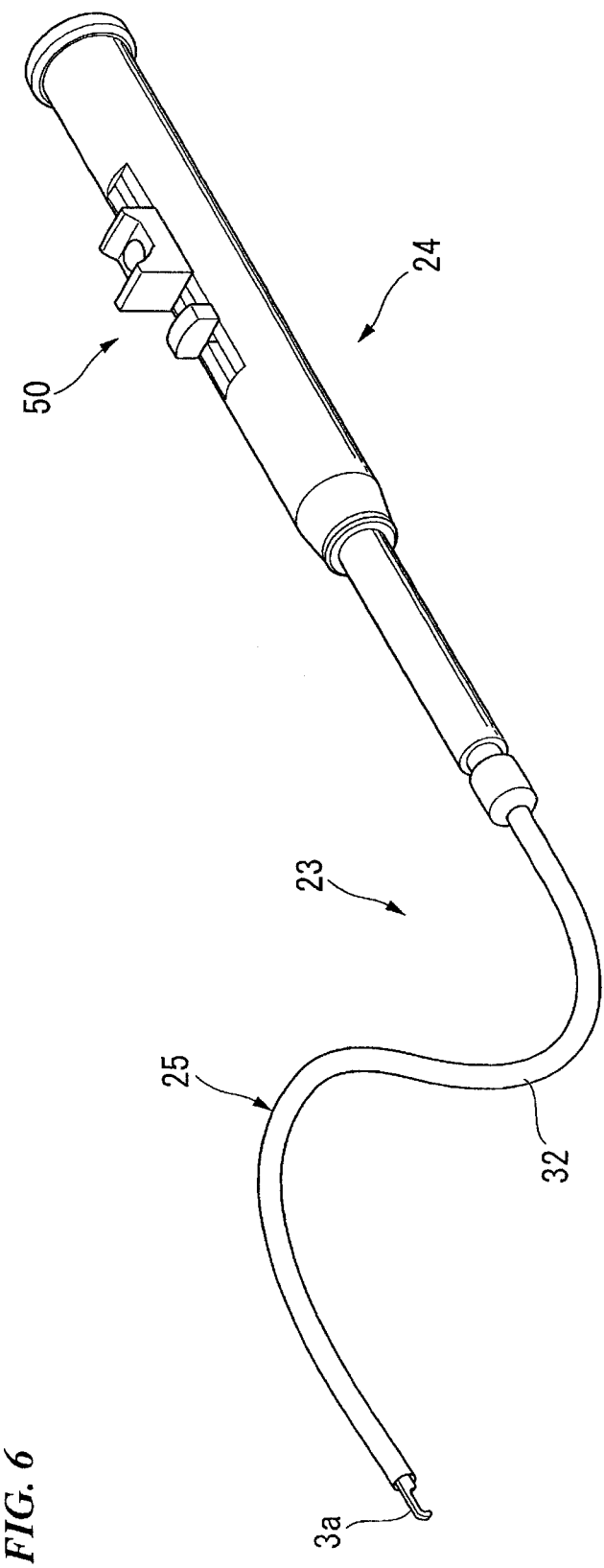
FIG. 6 is an overall view of the dissection instrument shown in FIG. 5.

Next, the dissection instrument 23 according to the second embodiment will be explained in detail using FIGS. 6 through 12. FIG. 6 shows an overall view of the dissection instrument 23 which is inserted into the endoscope inserted part 28 and the first sheath 22 as explained above. The tube 32 of the inserted part 25 is provided to the distal end side of the actuator 24, and a high-frequency hook 3a is provided in a manner to permit advancing and retracting from the opening at the distal end of the tube 32.

Figure 7:
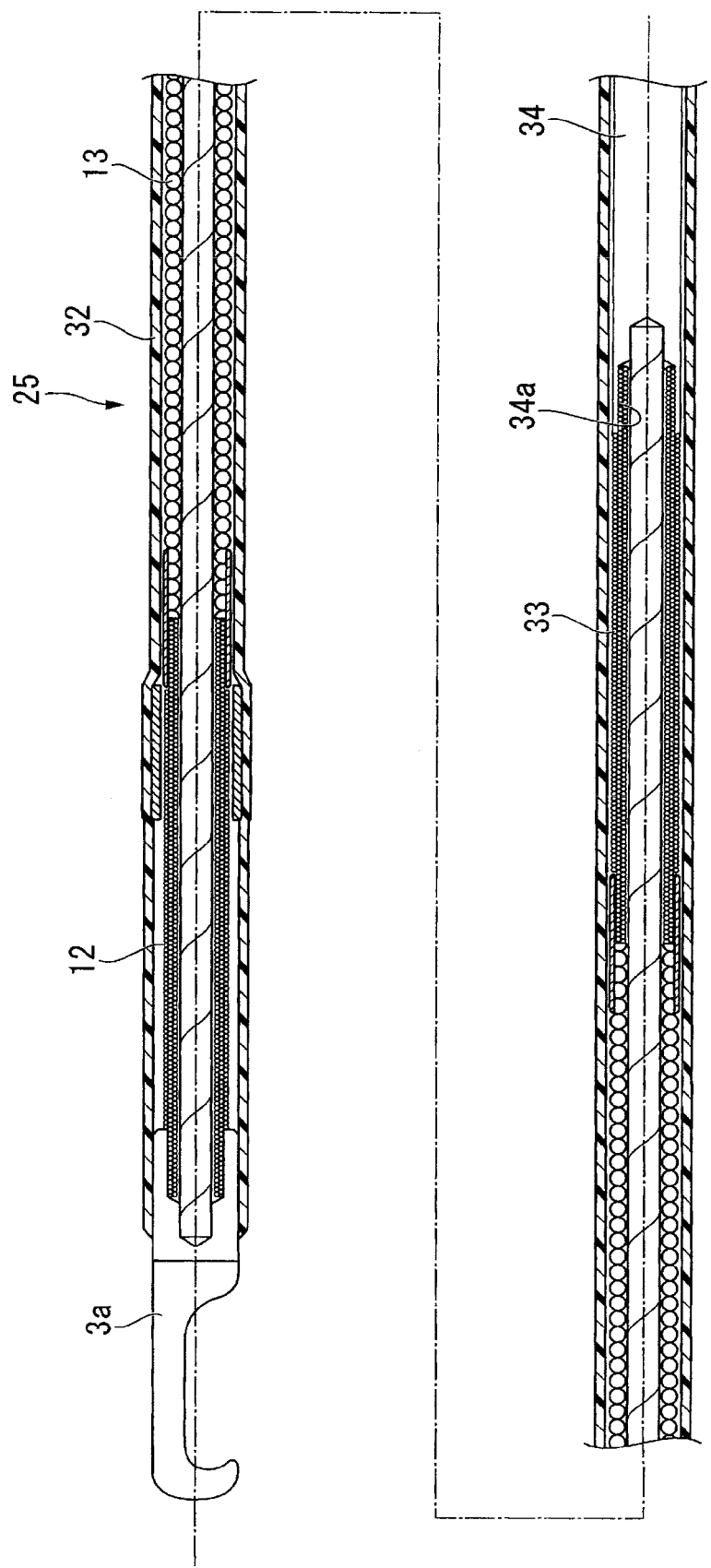
FIG. 7 is an essential component cross-sectional view showing the inserted part of the dissection instrument shown in FIG. 6.

The internal design of the dissection instrument 23 will now be explained using the cross-sectional views shown in FIGS. 7 and 8. First, the design of the shaft which is inserted into the tube 32 shown in FIG. 7 will be explained. A multiple layer coil, which is relatively flexible and having high rotation follow-up property of three-layer coil 12 for example, is connected by welding, etc. to the proximal end of the high-frequency hook 3a, and serves as a distal shaft. A multiple strand coil which is relatively rigid and has a high rotation follow-up property and, nine-strand coil 13 for example, is connected to the proximal end of the three-layer coil 12, and serves as an intermediate shaft. The nine-strand coil 13 is long, and its connection with the three-layer coil 12 is fixed by soldering, etc. at the step portions via the connecting tube 15 as explained above.

A multiple layer coil, which is relatively flexible and has high rotation follow-up property similar to that of the distal shaft, three-layer coil 33 for example, is connected to the proximal end of the long nine-strand coil 13, and serves as the proximal shaft. The connection between the nine-strand coil 13 and the three-layer coil 33, i.e., the proximal shaft, has the same structure as the connection between the nine-strand coil 13 and the three-layer coil 12, i.e., the distal shaft, and is connected by soldering when the connecting tube 15 is in a state of engagement with the step portions of the nine-strand coil 13 and the three-layer coil 33. The mutually connected three-layer coil 12, nine-strand coil 13 and three-layer coil 33 are together referred to as a "shaft".

The respective three-layer coils 12, 33 on the distal and proximal end sides are positioned at the distal end side bending part 28a of the endoscope inserted part 28 and the proximal end side bending part 22a of the first sheath 22 in the medical treatment endoscope 20.

The proximal end of the three-layer coil 33 on the proximal end side engages with the inside of a concavity 34a in an operating shaft 34, and is connected there by welding or soldering. This operating shaft 34 is rigid and extends inside the actuator 24 and is connected to the actuator 24 as described below.

Figure 8:
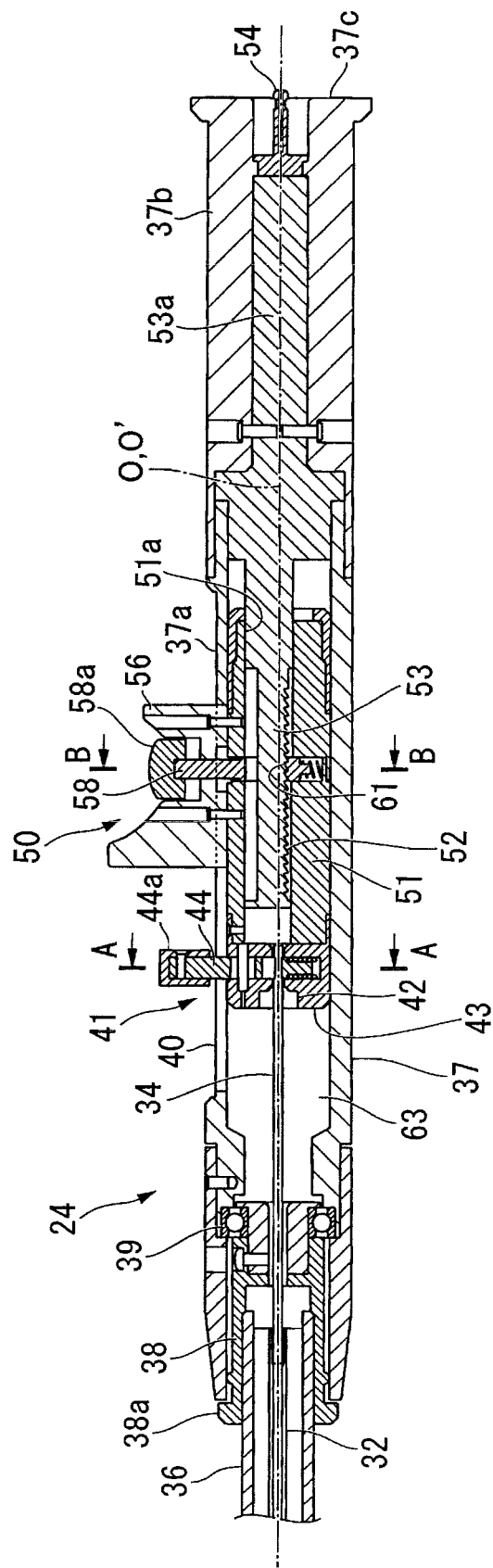
FIG. 8 is a cross-sectional view showing the actuator for the dissection instrument shown in FIG. 5.
Figure 9A:
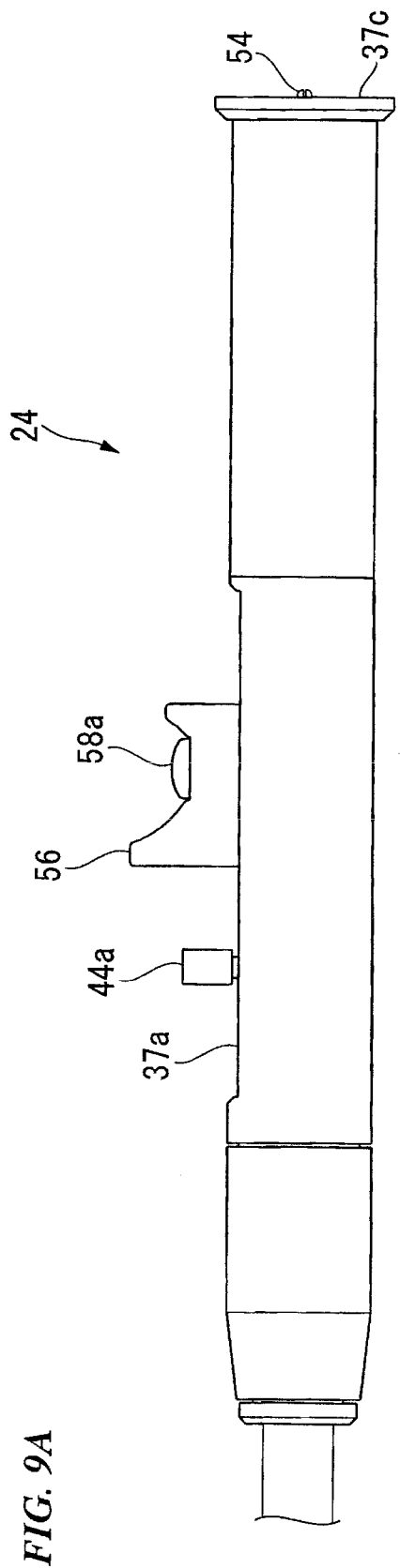
FIG. 9A is a lateral view of the actuator.
Figure 9B:
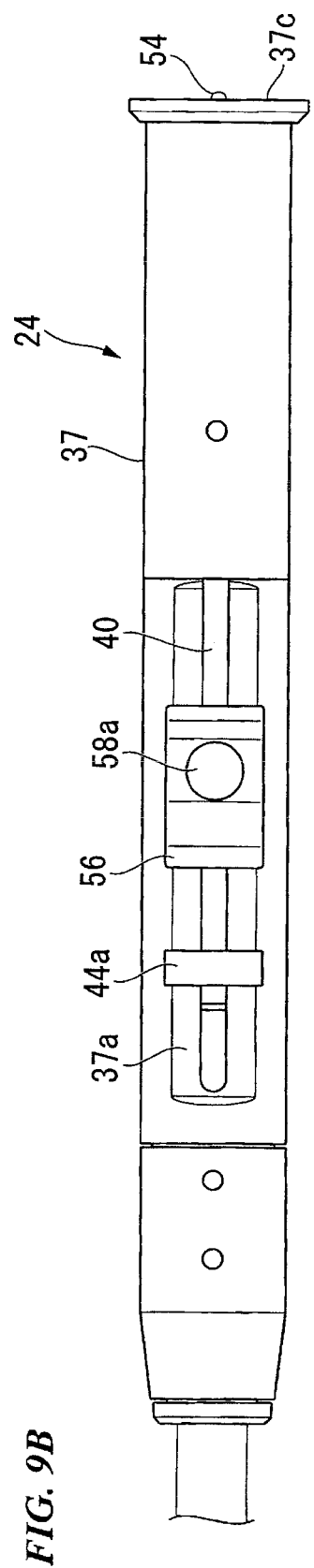
FIG. 9B is a planar view of the actuator.

In FIG. 8, the actuator 24 is provided with a main body 37 that is approximately tubular. In this actuator 24, the proximal part of the tube 32 passes through a tubular part 36. The proximal part of the tubular part 36 is provided at the distal end of the main body 37, and is attached to the inside of a cylindrical member 38 which is supported by the inside of the main body 37 to permit relative rotation. A flange 38a that projects outward in a radial direction from the distal end of the main body 37 is formed to the distal end of the cylindrical member 38.

The main body 37 of the actuator 24 is designed to enable rotation with respect to the cylindrical member 38 via axes 39 which are provided at the proximal part of the cylindrical member 38. A guide groove 40 is formed at a central area in the longitudinal direction of the main body 37, and extends along the longitudinal direction on a flat central upper surface 37a (see FIG. 9A, FIG. 9B). A fixing part 41 is disposed to enable sliding inside the main body 37 within the region of the guide groove 40. The fixing part 41 fixes the operating shaft 34 which passes through the cylindrical member 38 and extends to the proximal end side. The center axis O of the operating shaft 34 preferably coincides with the center axis O of the main body 37.

Figure 10A:
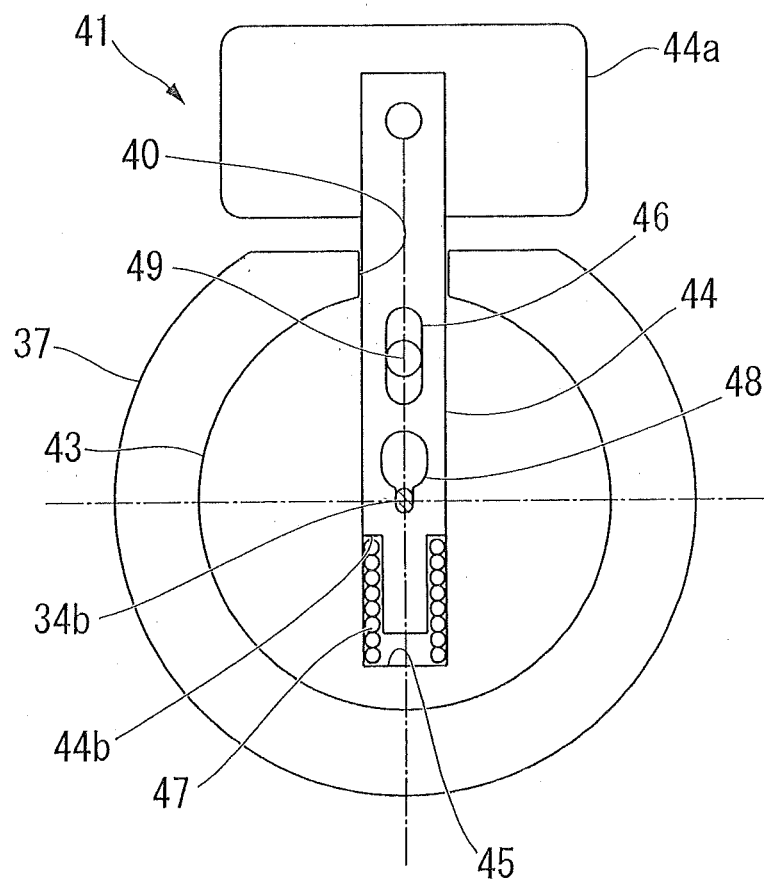
FIG. 10A is an expanded cross-sectional view along the line A-A of the fixing part in the actuator shown in FIG. 8.

The fixing part 41 shown in FIG. 8 and FIG. 10A has a first sliding part 43 that can slide an inner surface of the main body 37 and is provided with an internal through hole 42 that is formed in the direction of sliding. A fixing concavity 45 is formed to the first sliding part 43, perpendicular to the through hole 42. A fixed axis 44 which extends through the guide groove 40 of the main body 37 to outward is inserted in the fixing concavity 45 so as to be capable of moving in reciprocating motion (vertical motion). An actuator button 44a is provided to the head on the fixed axis 44, and a stepped part 44b is formed in the bottom part of the fixed axis 44. A coil spring 47, for example, is attached as an elastic member between the stepped part 44b and the bottom part of the fixing concavity 45. As a result, the fixed axis 44 is biased so as to project out from the guide groove 40. A long hole 46 is formed in the fixed axis 44, and a regulating pin 49 which is provided to the first sliding part 43 is inserted into this long hole 46. The extent of the reciprocating motion (vertical motion) of the fixed axis 44 is regulated by this long hole 46 and regulating pin 49.

Figure 10B:
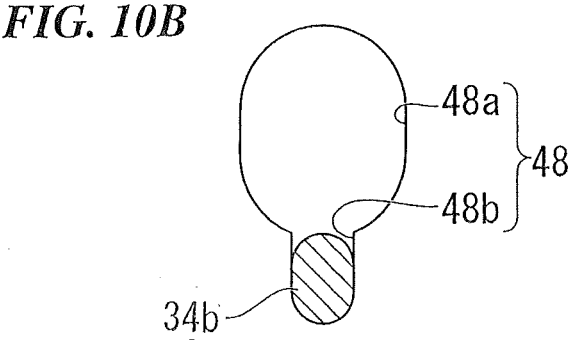
FIG. 10B is an expanded view of the operating shaft and the fixing hole in FIG. 10A.

Further, an approximately gourd-shaped fixing hole 48, in which a large diameter part 48a and a slit 48b communicate, is formed in the approximate center of the fixed axis 44 and is positioned on top of through hole 42. The base 34b of the operating shaft 34 is inserted into the fixing hole 48. This base 34b is formed to be approximately oval in cross-section so as to be capable of engaging with the slit 48b of the fixing hole 48, as shown in FIG. 10B.

Under ordinary conditions, the base 34b of the operating shaft 34 is engaged and fixed in place in the slit 48b of the fixing hole 48 due to the biasing force of the coil spring 47. The operating shaft 34 is designed so as to rotate integrally with the main body 37 around the center axis o of the operating shaft 34. As a result, it is possible to change the angle of the high-frequency hook 3a with respect to the diseased area K by rotating the main body 37. In addition, by pushing the operating button 44a of the fixed axis 44, the fixed axis 44 is moved toward the bottom of the fixing concavity 45 against the biasing force of the coil spring 47, so that the base 34b of the operating shaft 34 is moved from the slit 48b into the large diameter part 48a. The operating shaft 34 is thereby released from the main body 37.

In FIG. 8, an operating member 50 is provided adjacent to the fixing part 41. An approximately cylindrical second sliding part 51 to which the first sliding part 43 of the fixing part 41 is connected by a screw or the like is provided in the operating member 50. And these configures a integrally sliding member. These first and second sliding members 43,51 can be moved by sliding in a unitary manner within the main body 37. A through hole 51a is formed in the longitudinal direction within the second sliding part 51. As a support part, a ratchet member 53 including ratchet teeth 52 is disposed in a fixed manner inside the through hole 51a. The base 53a of the ratchet member 53 engages in a concavity at the proximal end portion 37b of the main body 37. A connector 54 which is exposed at the proximal end surface 37c of the main body 37 is attached to the rear of the base 53a of the ratchet member 53.

A knob 56 which projects outward passing through the guide groove 40 is provided to the second sliding part 51. An operating hole 57 is formed in the knob 56 and the second sliding part 51 extending in the direction perpendicular to the center axis O', and communicates with a through hole 51a. The operating axis 58 is inserted from the knob 56 side into the operating hole 57 so as to be capable of reciprocally moving (vertical motion) within specific limits.

Figure 11:
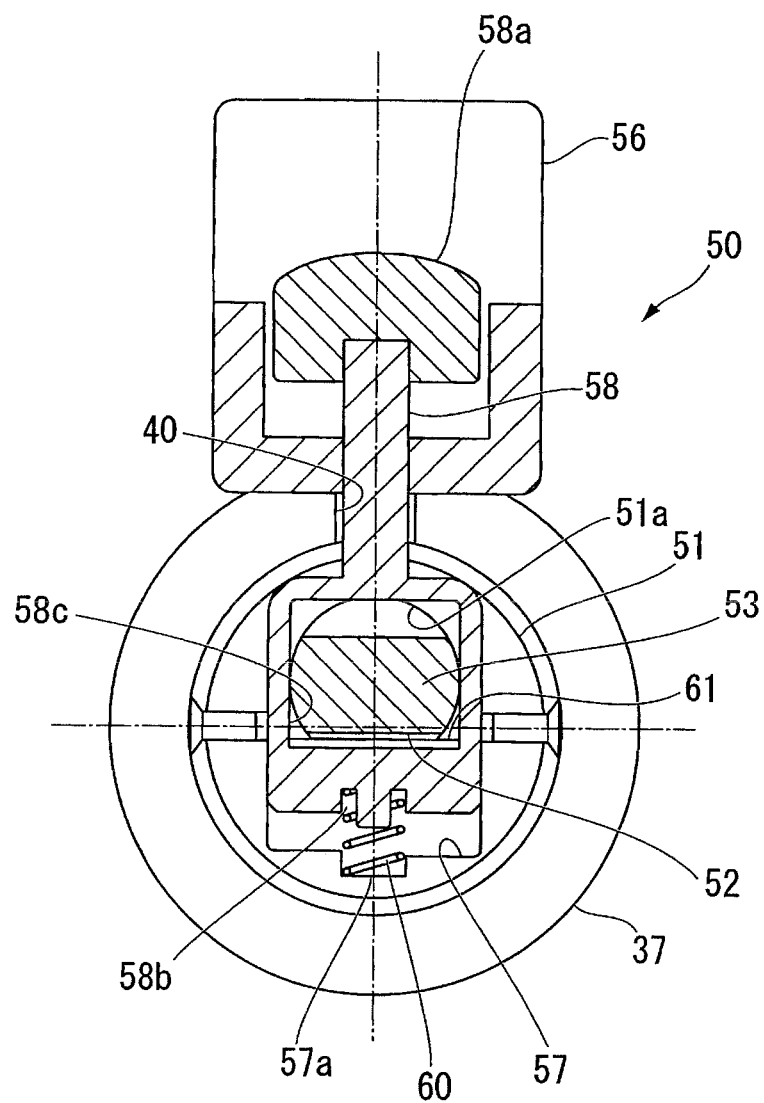
FIG. 11 is an expanded cross-sectional view along the line B-B of the operating member shown in FIG. 8

As shown in FIG. 11, the operating axis 58 is provided with an operating button 58a at its head, and a stepped part 58b at its bottom. The center portion of the operating axis 58 widens to an approximately square shape when seen in vertical cross-section, and a window 58c is formed penetrating internally. A coil spring 60 is attached in a compressed state in between the stepped part 58b that is provided to the bottom of the operating axis 58 and the step 57a that is provided at the bottom of the operating hole 57, coil spring 60 serving as an elastic member.

Figure 12:
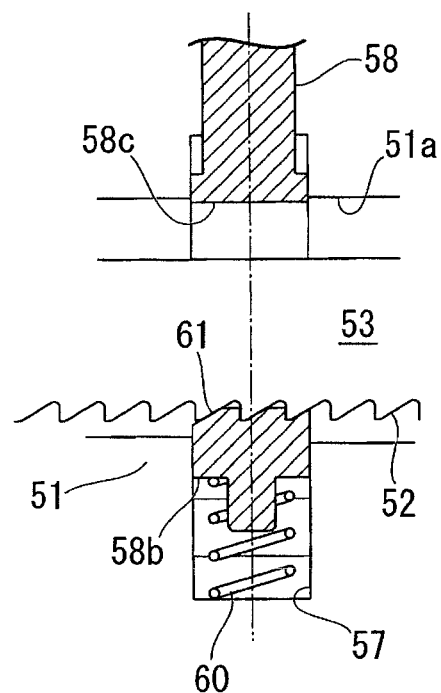
FIG. 12 is an expanded view of the ratchet mechanism shown in FIG. 8.
Figure 13:
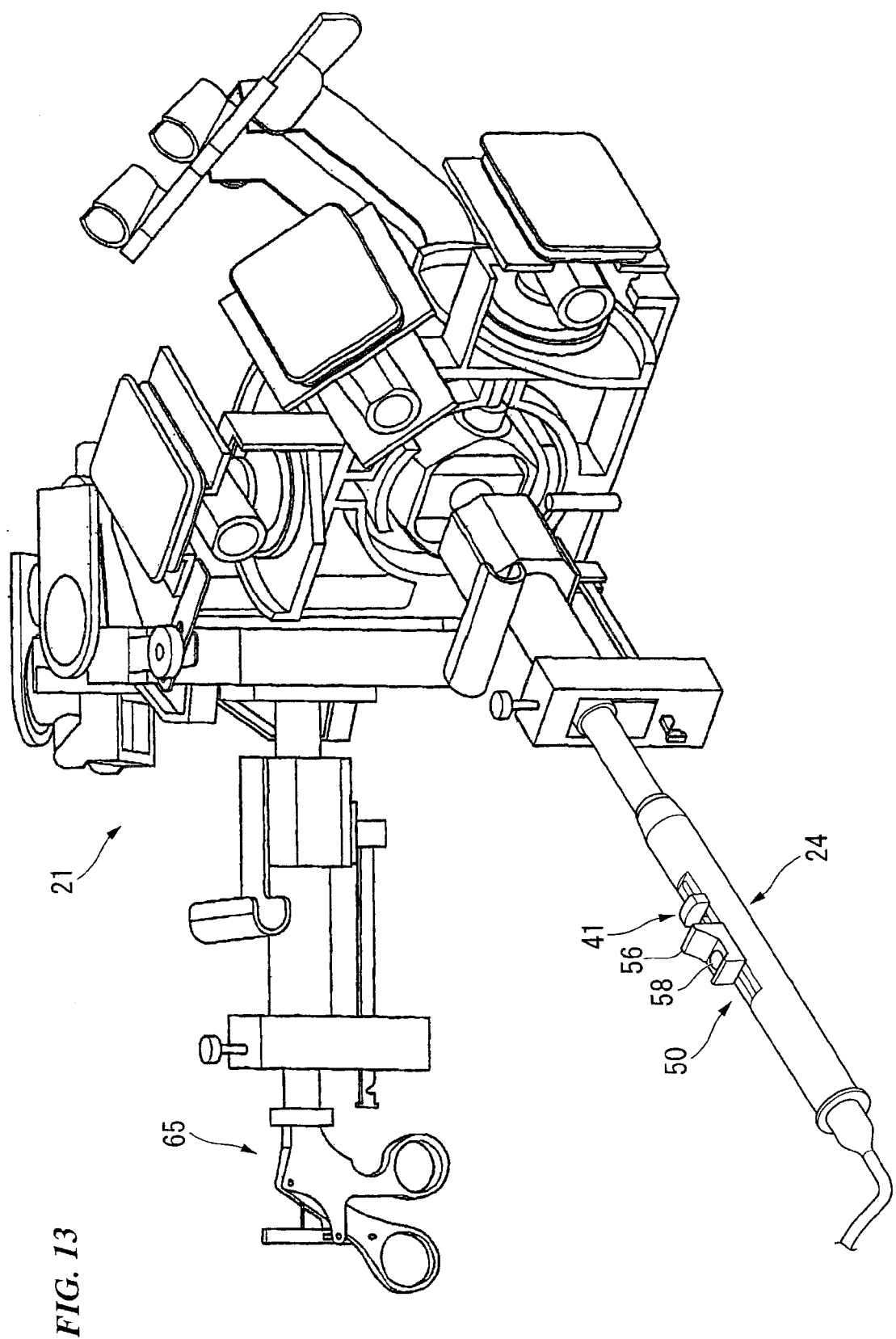
FIG. 13 is a perspective view of the actuator of the medical treatment endoscope.

The ratchet teeth 52 of the ratchet member 53 and the ratchet claw 61 that is provided to the window 58c form a ratchet mechanism in which they engage with one another in a state that the operating axis 58 is pushed upward under the biasing force of the coil spring 60 (see FIG. 12). The tooth profile of the ratchet teeth 52 is formed so that when engaged with the ratchet claw 61, for example, the second sliding part 51 which includes the ratchet claw 61 can move in one direction, forward for example, but movement in the opposite direction toward the proximal end is prohibited. Conversely, when the operating button 58a of the operating axis 58 is pushed in against the biasing force of the coil spring 60, the ratchet claw 61 moves away from the ratchet teeth 52. Note that it is also acceptable to provide the ratchet teeth 52 to the window 58c, and to provide the ratchet claw 61 to the ratchet member 53.

The ratchet member 53 attached to the connector 54; the operating axis 58; the coil spring 60; the second sliding part 51; the first sliding part 43 of the fixing part 41; the coil spring 47; and the fixed axis 44 are formed of a conductive member, and can transmit electricity to the high-frequency hook 3a via the operating shaft 34 and the shafts (various coils 12, 13, 33) which consist of conductive member as with above members. Further, by pushing the operating button 58a in the operating member 50, the ratchet claw 61 of the operating axis 58 can be detached from the ratchet teeth 52, thus interrupting current flow between them.

In a space 63 which is formed between the cylindrical member 38 and the ratchet member 53 inside the main body 37 of the actuator 24, the first sliding part 43 of the fixing part 41 and the second sliding part 51 of the operating member 50 are configured to slide integrally. When the ratchet claw 61 is detached from the ratchet teeth 52 by pushing the operating button 58a of the operating member 50, the knob 56 is advanced or retracted along the guide groove 40. As a result, the first sliding part 43 and the second sliding part 51 slides integrally in the internal space 63 inside the main body 37, and the high-frequency hook 3a can be advanced or retracted via the fixing part 41. By moving the knob 56 forward with the ratchet claw 61 in a state of engagement with the ratchet teeth 52, the hook 3a can be made to move in projecting direction in a state of conduction. In addition, the first and second sliding parts 43, 51 rotate integrally by rotating the main body 37 about center axis O', therefore, from the operating shaft 34 to the hook 3a rotates about the same axis.

Figure 16:
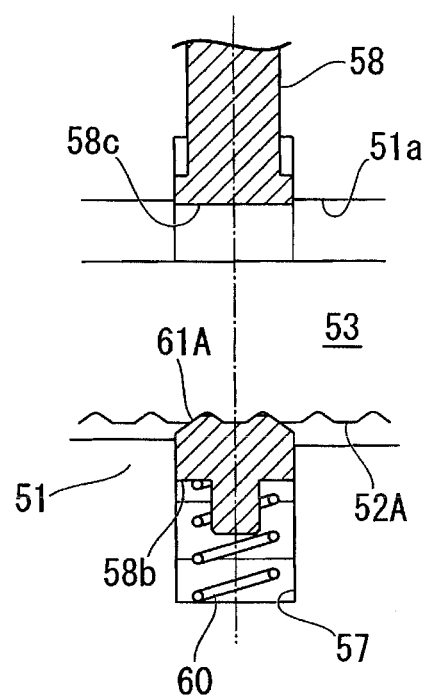
FIG. 16 is a view showing a modification of the ratchet mechanism shown in FIG. 12.

Note that FIG. 16 shows a modified example of the above-described ratchet mechanism. The ratchet teeth 52A and the ratchet claw 61A shown in FIG. 16 form a peaked tooth profile that permits movement of the second sliding part 51 in the advancing or retracting direction when engaged. As a result, the high-frequency hook 3a can be advanced or retracted with respect to the tube 32 without pushing an operating button 58a, by advancing or retracting the knob 56 when the ratchet teeth 52A and the ratchet claw 61A are maintaining a state of engagement, i.e., when maintaining a state of conduction.

The medical treatment endoscope 20 equipped with a dissection instrument 23 according to the second embodiment is provided with the above-described design. The operation method of the medical treatment endoscope 20 will now be described.

Figure 5:
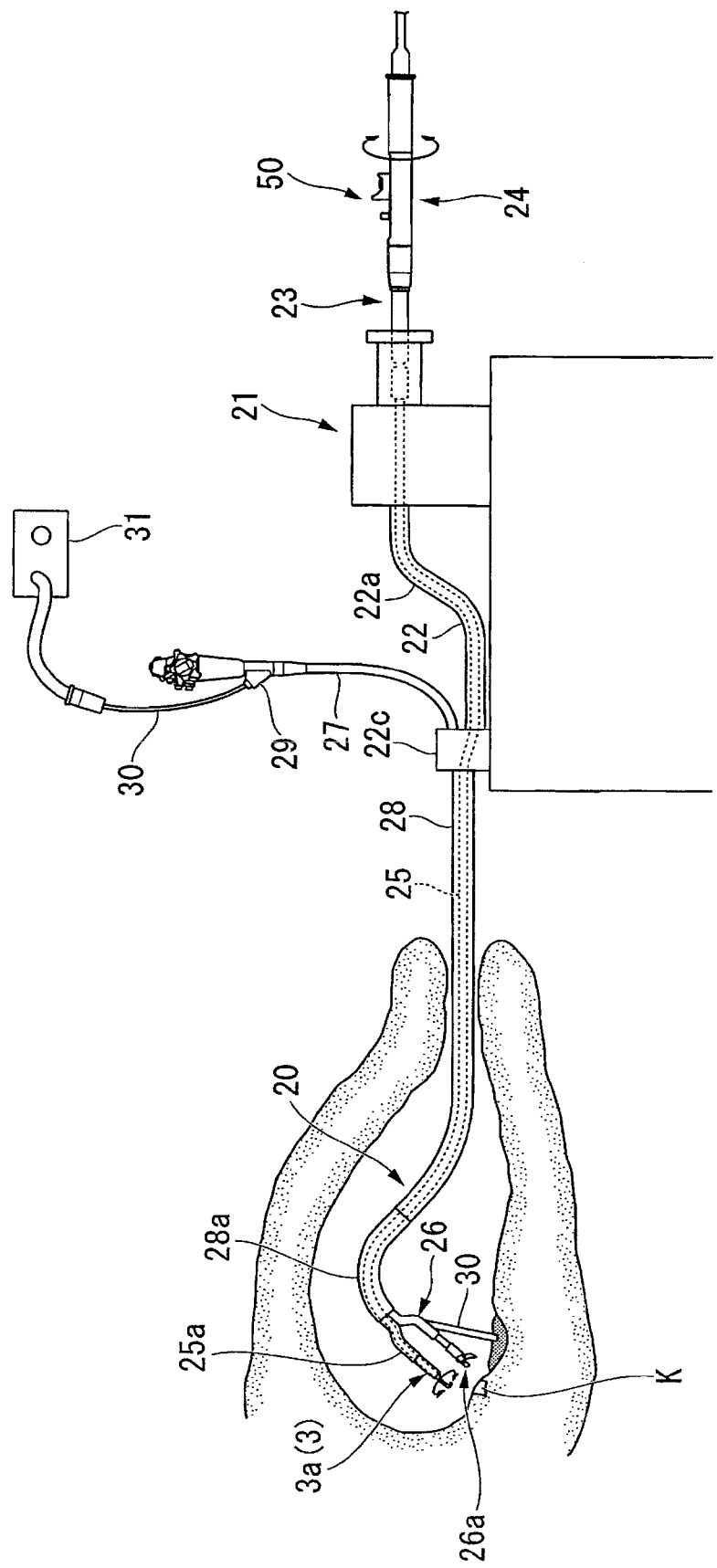
FIG. 5 is a view showing the state when a diseased area is treated with the medical treatment endoscope that includes a dissection instrument according to a second embodiment of the present invention.

First, the endoscope inserted part 28 of the medical treatment endoscope 20 is inserted into a body cavity as shown in FIG. 5. Dissection instrument 23 and gripping forceps 26, for example, are then inserted as treatment instruments into respective channels of the endoscope inserted part 28, and the front ends thereof are made to project out from the arms 25a, 26b. While moving the distal arms 25a, 26b by manipulating the actuator 21 of the medical treatment endoscope, a technician, carries out the procedure on the diseased area K, for example, by using his left hand to manipulate the actuator 65 of the gripping forceps 26 and using his right hand to manipulate the actuator 24 of the dissection instrument 23.

For example, the diseased area K is gripped in the jaws 26a of the gripping forceps 26. In the dissection instrument 23, the knob 56 of the actuator 24 along the guide groove 40 is moved forward (toward the high-frequency hook 3a side). As a result, with the ratchet teeth 52 and the ratchet claw 61 in a state of engagement, the second sliding part 51 and the first sliding part 43 of the fixing part 41, together with the ratchet claw 61, are moved forward through the internal space 63 of the main body 37, and the operating shaft 34, which is fixedly attached to the fixing part 41, moves forward.

The high-frequency hook 3a is advanced and projected from the distal opening of the tube 32 via the three-layer coil 33, the nine-strand coil 13, and the three-layer coil 12 inside the tube 32. In particular, of these coils 12, 13 and 33, the long nine-strand coil 13 is highly rigid, so that it can be advanced and retracted in high responsiveness.

When the high-frequency hook 3a does not have the desired orientation with respect to the diseased area K held by the jaws 26a of the gripping forceps 26, the main body 37 of the actuator 24 is rotated by the desired angle with respect to the cylindrical member 38 around the center axis O'. As a result, since the operating shaft 34 is fixed to a fixing part 41 which rotates in unison with the main body 37, the operating shaft 34 is also rotated around the center axis O. The highly flexible respective three layer coils 33,12 are positioned at bending parts 22a, 28a, so that the orientation of the high-frequency hook 3a can be adjusted to the specific angle through the communication of the rotation via the respective coils 33,13,12 which have high rotation follow-up property.

A power source cord, which is not shown in the figures, is attached to the connector 54 of the actuator 24. A high-frequency current can be communicated with certainty to the high-frequency hook 3a at the distal end from the connecting part 54 at the rear end, via the ratchet member 53, the ratchet teeth 52 and ratchet claw 61 which are in a state of engagement, the second sliding part 51, the first sliding part 43, the operating shaft 34, the shafts (various coils 33, 13, 12), and the like. For this reason, the diseased area K gripped by the jaws 26a of the gripping forceps 26 can be incised using the high-frequency hook 3a.

Note that when pulling the high-frequency hook 3a into the tube 32, the knob 56 may be retracted along the guide groove 40 while pushing the operating button 58a of the actuator 24. Further, in the ratchet mechanism according to the modified example shown in FIG. 16, it is not necessary to push the operating button 58a when pulling in the hook 3a.

Further, as necessary during treatment, the irrigation and suction tube 30 consisting of a flexible tube may be inserted via the second sheath 27, and passed though the endoscope inserted part 28, so that the main opening 30a at its distal end is projected into the vicinity of the diseased area K. Further, when there is hemorrhage or the like around the diseased area K, irrigating fluid may be expelled from the irrigation and suction device 31 to wash the area, and fluid remaining inside the body may be suctioned out. In particular, side openings 30b are formed near the main opening 30a at the distal end of the irrigation and suction tube 30, so that irrigation and suction can still be carried out via these side openings 30b even if the main opening 30a at the distal end is blocked by coming into contact with the body wall. Note that there is no connecting component at the distal end of the irrigation and suction tube 30, thus there is no concern about such components falling off.

In the dissection instrument 23 according the second embodiment as described above, highly flexible respective three-layer coils 12,33 within the tube 32 are disposed to the distal end side bending part 28a of the endoscope inserted part 28 and the proximal end side bending part 22a of the first sheath 22. As a result, rotation can be sufficiently transmitted with no effect on the respective bending parts 28a,22a. Moreover, the center region, excluding the short both ends, of the three coils 12, 13, 33 that are connected in the longitudinal direction, is composed of the long nine-strand coil 13. As a result, when advancing and retracting the hook 3a, the nine-strand coil 13 can be retracted or advanced in high responsiveness without stretching or contracting. In addition, in the conventional art, when the connector 54 and the operating shaft 34 are connected with a cord or the like inside the actuator 24, there is a possibility that a disconnection could easily occur due to the operation which moving the operating shaft 34 advanced or retracted or the like. However, in the second embodiment, the conduction and cutoff of current to the high-frequency hook 3a at the distal end can be cared out by the ratchet mechanism that is provided inside the actuator 24, so that disconnection hardly occurs.

Figure 17:
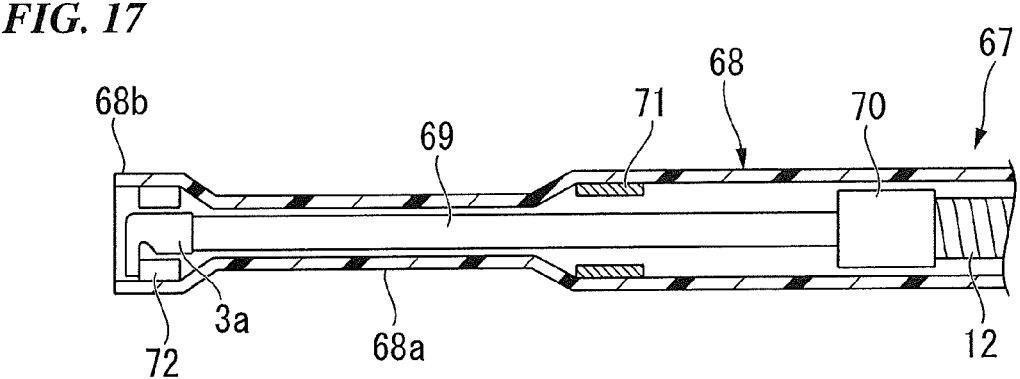
FIG. 17 is a partial cross-sectional view showing a first modification of the distal end of the inserted part.
Figure 18:
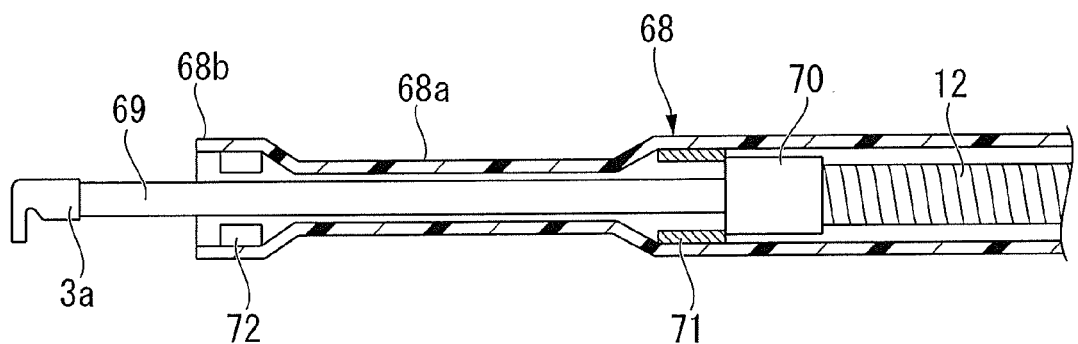
FIG. 18 is a view showing an arrangement in which the hook in FIG. 17 is projected out.

Next, an example of a modified example of the dissection instrument 1,23 as the endoscope treatment instrument will be explained using FIGS. 17 through 19. In the dissection instrument 67 according to the first modified example shown in FIGS. 17 and 18, the distal end of the tube 68 extends further forward than the distal end of the three-layer coil 12 which serves as the distal shaft, and there is formed an opening 68b, the diameter of which is widened by means of a small diameter part 68a which has been formed with a small diameter. In addition, a rigid rod-shaped electrode extension 69 which connects the three-layer coil 12 and the high-frequency hook 3a is disposed inside the small diameter part 68a. The electrode extension 69 forms an electrical single wire, having a length of 100 mm, for example.

A first stopper 71 for preventing the connecting part 70 between the electrode extension 69 and the three-layer coil 12 from projecting forward is provided to the inner peripheral surface of the tube 68. The tube 68 is positioned on the proximal end side of the small diameter part 68a, and has a larger diameter than the small diameter part 68a. A second stopper 72 for preventing the high-frequency hook 3a from being pulled into the tube 68 is provided to the inner surface of the expanded diameter opening 68b of the tube 68.

In this modified example, during treatment, etc., the tube 68 which is projected out from the arm 25a provided to the medical treatment endoscope 20, is reinforced by the electrode extension 69 that is positioned internally. During dissection operations, the actuator 24 is manipulated to advance the three-layer coil 12, i.e., the distal shaft, within the tube 68 until the connecting part 70 comes into contact with the first stopper 71 and the electrode extension 69 is projected out from the distal opening 68b of the tube 68. Dissection is then performed using the hook 3a (see FIG. 18).

Accordingly, as a result of providing a small diameter part 68a extending from the tube 68, and providing the electrode extension 69 internally, in the dissection instrument 67 according to this modified example, the tube 68 can be made thinner, facilitating advancing and retracting. Further, since reinforcement can be provided by the electrode extension 69, bending can be prevented, and the operation of dissection the tissue using the hook 3a can be carried out easily.

Figure 19:
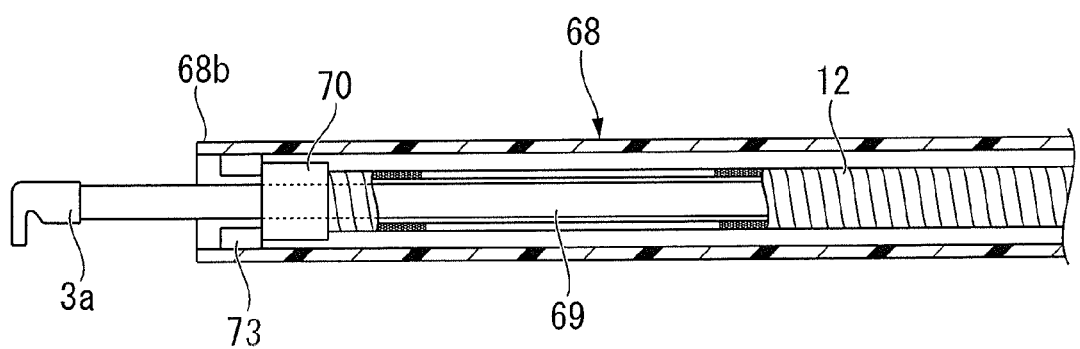
FIG. 19 is a partial cross-sectional view showing a second modification of the distal end of the inserted part.

Next, in the second modification shown in FIG. 19, the tube 68 is formed extending so as to cover the electrode extension 69, and a stopper 73 is provided on the inner surface of the distal opening 68b. The electrode extension 69 extends inside the three-layer coil 12. When the hook 3a is advanced using the actuator 24, the three-layer coil 12 advances until the connecting part 70 comes into contact with the stopper 73 inside the tube 68, so that the hook 3a can be projected out. In this case, the electrode extension 69 is covered by the three-layer coil 12, i.e., the distal shaft, thus increasing the rigidity in this region and making it more difficult for bending to occur. The stopper 73 also prevents the hook 3a from being pulled inside.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

For example, single strand multiple layer coils 12, 33 were employed as distal and proximal shafts, respectively, in the above-described embodiment, however, it is also acceptable to form the multiple layer coils 12, 33 using multiple strand coils. In this case, it is necessary to make the metal wires thinner, however flexibility can be maintained due to the use of a multiple layer coil.

In addition, the various embodiments and modifications described above employed a three-layer coil 12, 33 for the first coil sheath, however, it is also acceptable to employ a multiple layer coil for these, with the number of coil layers being optional. Similarly, while a nine-strand coil 13 was employed as the second coil sheath, if a multiple strand coil is employed, then the number of aligned metal wires is optional. These form the communicating member.

The invention is not to be considered as being limited by the foregoing description, and is only limited by the scope of the appended claims.

The invention claimed is:
1. An endoscope treatment instrument comprising:
a flexible transmitting member which is inserted into an outer sheath so as to retract and advance with respect to the outer sheath;
a treatment portion that is attached to a distal end of the transmitting member; and
an actuator which is attached to a proximal end of the transmitting member and is for operating the treatment portion, wherein,
the endoscope treatment instrument is designed to transmit an action of the actuator to the treatment portion via the transmitting member, and wherein
the transmitting member is configured by connecting a first coil sheath having a first structure including a multiple layer coil for improving a rotation follow-up property around a longitudinal axis of the transmitting member, and a second coil sheath having a second structure including a multiple strand coil for improving the rotation follow-up property around the longitudinal axis,
the first coil sheath is connected on the treatment portion,
the second coil sheath is connected on a proximal end of the first coil sheath,
the first coil sheath has a higher flexibility than the second coil sheath by being provided with the first structure, and the second coil sheath has a higher response to move in an advance or retract direction than the first coil sheath by being provided with the second structure.

2. The endoscope treatment instrument according to claim 1, further comprising:
a third coil sheath having the first structure,
wherein the second coil sheath is positioned between the first coil sheath and the third coil sheath, and
the third coil sheath has a higher flexibility than the second coil sheath by being provided with the first structure.

3. The endoscope treatment instrument according to claim 1, wherein the multiple layer coil is formed of a single strand coil or a multiple strand coil.

4. The endoscope treatment instrument according to claim 1, wherein the multiple strand coil is a single layer coil.

* * * * *